"

US010487070B2

(12) United States Patent
Bertolini et al.

(10) Patent No.: US 10,487,070 B2
(45) Date of Patent: Nov. 26, 2019

(54) PROCESS FOR PREPARING INTERMEDIATES USEFUL IN THE SYNTHESIS OF ANTIFUNGAL DRUGS

(71) Applicant: OLON S.P.A., Rodano MI (IT)

(72) Inventors: Giorgio Bertolini, Rodano (IT); Corrado Colli, Rodano (IT); Mara Sada, Rodano (IT); Federica Colombo, Mariano Comense (IT)

(73) Assignee: OLSON S.P.A., Rodano (IT)

( * ) Notice: Subject to any disclaimer, the term of this patent is extended or adjusted under 35 U.S.C. 154(b) by 0 days.

(21) Appl. No.: 16/093,176

(22) PCT Filed: Mar. 23, 2017

(86) PCT No.: PCT/IB2017/051687
§ 371 (c)(1),
(2) Date: Oct. 12, 2018

(87) PCT Pub. No.: WO2017/178909
PCT Pub. Date: Oct. 19, 2017

(65) Prior Publication Data
US 2019/0119244 A1 Apr. 25, 2019

(30) Foreign Application Priority Data
Apr. 13, 2016 (IT) .............................. UA2016A2545

(51) Int. Cl.
*C07D 401/06* (2006.01)
*C07D 491/10* (2006.01)
*A61P 31/10* (2006.01)

(52) U.S. Cl.
CPC ......... *C07D 401/06* (2013.01); *C07D 491/10* (2013.01); *A61P 31/10* (2018.01)

(58) Field of Classification Search
CPC .......................... C07D 401/06; C07D 491/10
USPC ........................................................ 546/18
See application file for complete search history.

(56) References Cited

U.S. PATENT DOCUMENTS

| 5,292,973 | A * | 3/1994 | Fukumoto | C07C 17/2635 568/14 |
| 2004/0167166 | A1* | 8/2004 | Alberati-Giani | C07D 211/58 514/317 |
| 2012/0309771 | A1* | 12/2012 | Park | A61K 31/4196 514/256 |
| 2013/0150586 | A1* | 6/2013 | Mimura | C07D 401/06 546/210 |
| 2017/0129874 | A1* | 5/2017 | Gangavaram | C07D 401/06 |

FOREIGN PATENT DOCUMENTS

| EP | 2612859 | 7/2013 |
| EP | 3091007 | * 11/2016 |
| WO | 9426734 | 11/1994 |
| WO | 2011099804 | 8/2011 |

OTHER PUBLICATIONS

Zhao; Chinese Journal of Medicinal Chemistry 2006, 16, 150-153. (Year: 2006).*
Ogura; Chem. Pharm. Bull. 1999, 47, 1417-1425. (Year: 1999).*
Tamura; J. Org. Chem. 2014, 79, 3272-3278. (Year: 2014).*
Wang; Chapter 617: "Tebbe Olefination", in Comprehensive Organic Name Reactions and Reagents, Wiley, 2010, pp. 2753-2757. (Year: 2010).*
Ogura H et al.Chemical and Pharmaceutical Bulletin, Pharmaceutical Society of Japan, JP vol. 47, No. 10, 1999, pp. 1417-1425.
Keiji Tamura et al., Journal of Organic Chemistry, vol. 79, Mar. 17, 2014, pp. 3272-3278.
International Search report and written opinion dated Jun. 8, 2017 for PCT/IB2017/051687.
International Preliminary Report in Patentability dated Oct. 25, 2018 for PCT/IB2017/051687.
Search Report dated Aug. 19, 2016 for Italian Priority Application No. IT 20160000379242.

* cited by examiner

*Primary Examiner* — Daniel R Carcanague
(74) *Attorney, Agent, or Firm* — Silvia Salvadori

(57) ABSTRACT

Subject-matter of the invention is a process for preparing intermediates useful in the synthesis of drugs, for example antifungal drugs, such as efinaconazole. Subject-matter of the invention are also such novel synthesis intermediates and the use thereof.

10 Claims, 6 Drawing Sheets

Mass detected by UPLC at the retention time of the peak of compound of formula (IV)
(above) and compound of formula (V) in hydrated form (below)

PROCESS FOR PREPARING INTERMEDIATES USEFUL IN THE SYNTHESIS OF ANTIFUNGAL DRUGS

This application is a U.S. national stage of PCT/IB2017/051687 filed on 23 Mar. 2017, which claims priority to and the benefit of Italian Application No. UA2016A002545 filed on 13 Apr. 2016, the contents of which are incorporated herein by reference in their entireties.

TECHNICAL BACKGROUND

Efinaconazole is the international non-proprietary name of compound (2R,3R)-2-(2,4-difluorophenyl)-3-(4-methylene-1-piperidinyl)-1-(1H-1,2,4-triazol-1-il)-2-butanol, having formula (I):

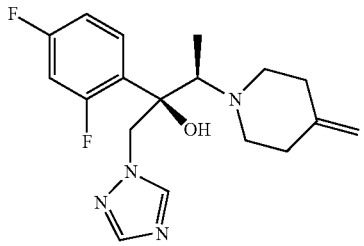

(I)

Efinaconazole is an antifungal drug, generally used in the treatment of onychomycosis.

Other molecules with antifungal activity are also known, having structure similar to that of efinaconazole, for example those described in WO2011/099804.

EP2612859 describes a synthesis of efinaconazole according to the following scheme

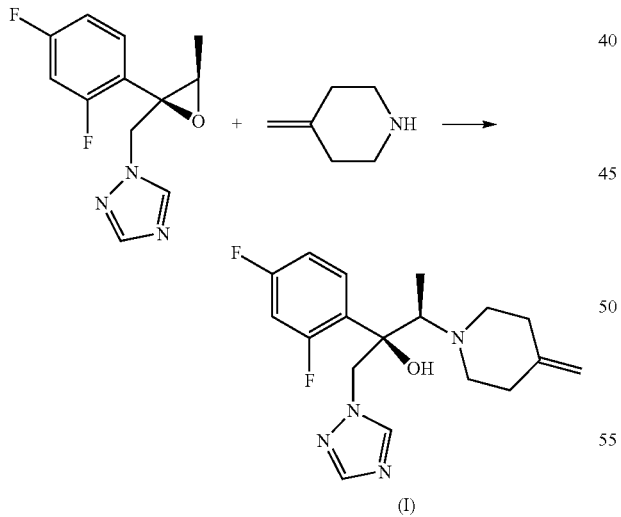

Reproducing such a synthesis involves problems, in particular due to the difficult availability of 4-methylenpiperidine and the volatility thereof, because of which it is possible that said compound evaporates during the long reaction time. Furthermore, the Applicant of the present application tried to reproduce some of the examples described in EP2612859, however without reproducibly obtaining the good yields and purities indicated in said document itself and moreover having to work in a pressure reactor to avoid the evaporation of 4-methylenpiperidine.

Because of these drawbacks, it is understood that there is a need to find novel syntheses of efinaconazole that give good results in terms of yield and purity and are also industrially pursuable, without the need to resort to complex equipment.

SUBJECT-MATTERS OF THE INVENTION

It is an object of the invention to provide novel intermediates particularly useful, but not only, in the synthesis of drugs, for example in the synthesis of efinaconazole or salts thereof or other antifungal drugs.

It is another object of the invention to provide a process for preparing said novel intermediates.

It is another object of the invention to provide a novel process of efinaconazole or salts thereof, in particular a process that could be feasible on an industrial scale.

DESCRIPTION OF THE INVENTION

According to one of its aspects, subject-matter of the invention is a process for preparing novel intermediate compounds particularly useful, but not only, in the synthesis of efinaconazole or salts thereof and other antifungal drugs, comprising the following scheme (A)

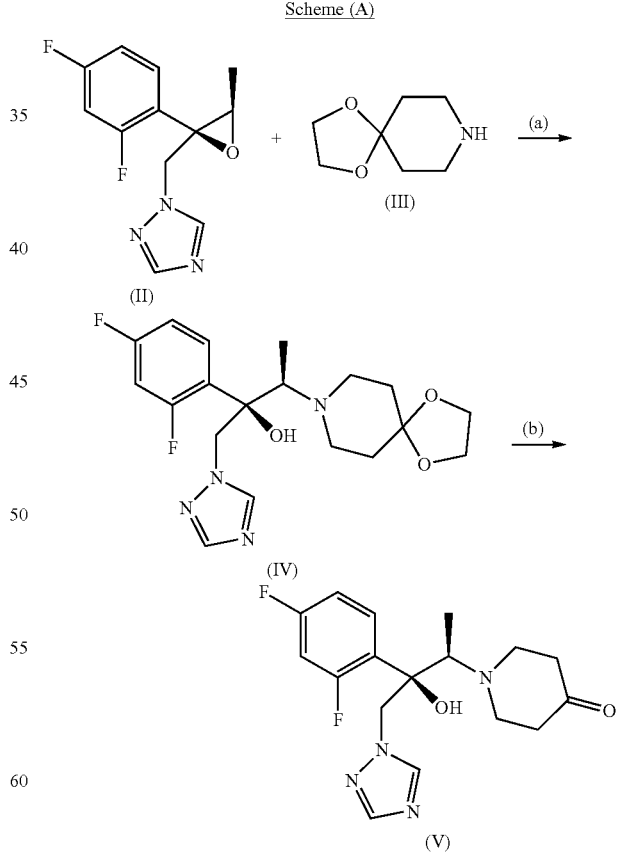

In particular, the process comprises reacting the compound of formula (II) with 1,4-dioxa-8-azaspiro[4.5]decane of formula (III) and subsequently hydrolyzing, in acidic environment, the so-obtained compound of formula (IV) to give the compound of formula (V).

The compounds of formula (II) and (III) are known and commercially available compounds. In particular, the compound of formula (III) is a very common and cheap raw material. Furthermore, the compound of formula (III) is less volatile than 4-methylenpiperidine used in the known synthesis reported above and, for this reason, it is more user friendly in chemical reactions.

The compounds of formula (IV) and (V), salts, hydrates and solvates thereof, as well as the hydrated form as geminal diol of the compound of formula (V), are novel compounds and constitute a further subject-matter of the present invention; another subject-matter of the invention is also their use as synthesis intermediates, in particular in the synthesis of antifungal drugs, for example in the synthesis of efinaconazole of formula (I) or salts thereof.

In the process of scheme (A), step (a) can also be carried out without solvents or advantageously in the presence of a solvent, such as a lower $C_1$-$C_4$ alcohol, water, acetonitrile, etc., or in a solvent mixture.

According to an advantageous embodiment, step (a) is carried out in a mixture of a lower $C_1$-$C_4$ alcohol and water, advantageously in a mixture of ethanol and water. According to a preferred embodiment, the solvent of step (a) is constituted by a mixture of ethanol and water, wherein water is present from 20 to 75% (v/v) with respect to ethanol, preferably from 20 to 50%, for example a mixture containing about 25% water and about 75% ethanol.

The reaction temperature of step (a) is from ambient temperature to the reflux temperature of the reaction mixture, preferably between 50° C. and the reflux temperature, even more preferably at the reflux temperature.

Depending on the operating temperature, the reaction is completed in more or less time. At lower temperatures a cleaner product is obtained, but the reaction is completed in a longer time; its development can anyway be checked by the skilled in the art by conventional techniques, for example by known chromatographic techniques.

If desired it is possible to carry out the reaction under pressure at higher temperatures, for example around 110° C.

The compound of formula (IV) can be isolated according to known techniques, for example by extraction or filtration and is obtained with optimal yield and purity. The compound of formula (IV) doesn't need any purification and can be used directly for the reaction of step (b).

Step (b) provides for the simple hydrolysis of the compound of formula (IV) in acidic environment, for example in the presence of an aqueous solution of an inorganic acid, advantageously in the presence of aqueous hydrochloric acid.

The reaction temperature of step (b) is from ambient temperature to the reflux temperature of the reaction mixture, preferably between 50° C. and the reflux temperature, even more preferably around 80° C.

The reaction is completed in a few hours, for example in 5-8 hours, and its development can be checked by the art technician by conventional techniques, for example by known chromatographic techniques.

The compound of formula (V) is isolated according to techniques well-known to the skilled in the art, for example by extraction in an organic solvent, such as an aromatic solvent or a chlorinated solvent, or a solvent mixture and by evaporating such solvents.

The compound of formula (V) is obtained with optimal yield and purity, as it will be shown in the Experimental Section.

According to a preferred embodiment, the process of the invention is made by reacting the compound of formula (II) with the compound of formula (III) in a solvent mixture containing about 25% water and about 75% ethanol, at the reflux temperature of the reaction mixture; subsequently, the compound (IV) is converted into compound (V) by acid hydrolysis, advantageously by heating in aqueous hydrochloric acid; said compound (V) is preferably isolated from the aqueous phase by extracting in one or more organic solvents according to known techniques. Details of the process of the invention described above are provided in the Experimental Section of the present description, as well as the characterization of the two novel compounds of formula (IV) and (V).

As mentioned, the compounds of formula (IV) and (V) can be used as synthesis intermediates, in particular in the synthesis of antifungal drugs, for example in the synthesis of efinaconazole or salts thereof.

According to another of its aspects, subject-matter of the invention is a process for preparing efinaconazole of formula (I) comprising subjecting the compound of formula (V) to a Wittig reaction, according to methods known in the art.

In order to carry out the Wittig reaction it is possible, for example, to react the compound (V) with a Wittig reagent, advantageously a phosphonium ylide, in the presence of an organic solvent. Then, the compound of formula (I) can be isolated according to known procedures and possibly converted in one of its salts. Alternatively, it is possible to convert the compound of formula (V) into efinaconazole of formula (I) by the McMurry reaction, itself also in the reaction conditions known to the skilled in the art.

Then, the so-obtained compound of formula (I) can be isolated according to known procedures and possibly converted in one of its salts.

Some detailed examples of the reactions reported above are provided in the Experimental Section of the present description.

Alternatively, it is possible to convert the compound of formula (V) into efinaconazole of formula (I) by the Tebbe's olefination reaction well known to the skilled in the art, providing for the use of a titanocene-trimethyl aluminum complex. Subject-matter of the invention, according to another of its aspects, is a process for preparing efinaconazole comprising carrying out the steps (a) and (b) described above and subsequently converting the compound of formula (V) in efinaconazole. From the above and the experimental data provided here below, the process of the invention clearly allows obtaining efinaconazole and two novel synthesis intermediates in a simple, economically acceptable and industrially feasible way.

The use of the compound of formula (IV) and/or the compound of formula (V) for the preparation of antifungal drugs, for example for the preparation of efinaconazole or salts thereof, constitutes a further aspect of the invention.

In fact such compounds are very versatile; in particular the compound of formula (V) carries a keto group on the piperidine allowing the easy introduction of several substituents. For this reason, said compounds are useful as synthesis intermediates in the preparation of the compounds of formula (I')

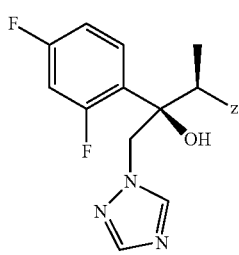

(I')

wherein Z is a piperidine, a substituted piperidine or a piperidine bearing double bonds within the ring, said piperidine being linked to the remainder part of the molecule through its nitrogen atom.

By way of example, starting from the intermediates compounds of the invention, preferably from the compound of formula (V), the compounds described in WO94/26734, WO2011/099804 and Chem. Pharm. Bull. 47(10), 1417-1425 (1999) can be synthesized.

For example, compounds having the following general formulae (A), (B) and (C) can be prepared:

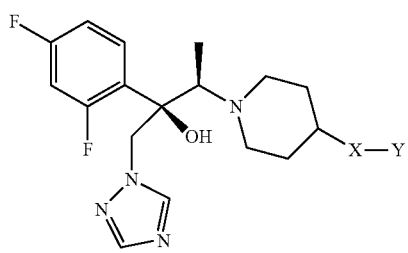

(A)

wherein X is —O—, —NR$_1$— or —CH$_2$—; R$_1$ is an hydrogen atom, or C$_1$-C$_6$ alkyl group; and Y is an aryl group, preferably phenyl, not substituted or substituted with one or more substituents selected from an halogen atom, a CF$_3$ group, a CN group and a C$_1$-C$_6$ alkyl group;

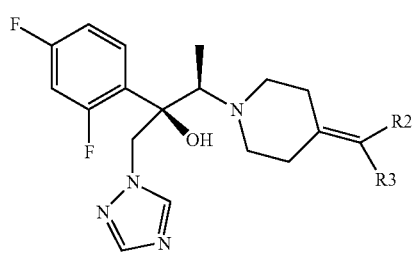

(B)

wherein R$_2$ and R$_3$ can each independently be an hydrogen atom, C$_1$-C$_6$ alkyl group or an aryl group, preferably not substituted or substituted phenyl;

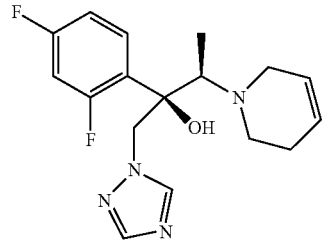

(C)

The use of the compounds of formula (IV) and (V) for the preparation of all of the molecules mentioned above constitutes a further subject-matter of the invention. Thus subject-matter of the invention, according to another of its aspects, is the use of the compound of formula (IV) and/or the compound of formula (V) in the preparation of the following molecules of formula (VI), (VII), (VIII), (IX) and (X):

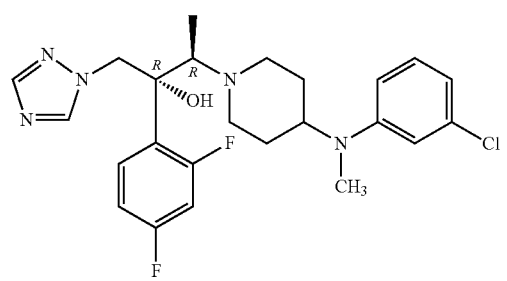

(VI)

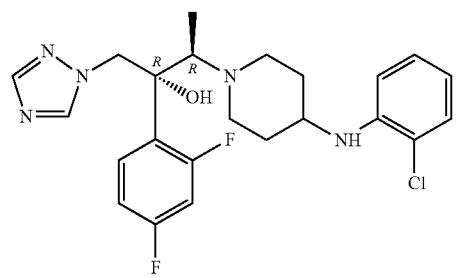

(VII)

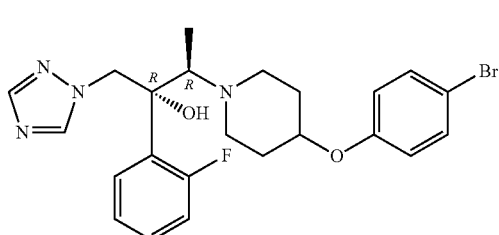

(VIII)

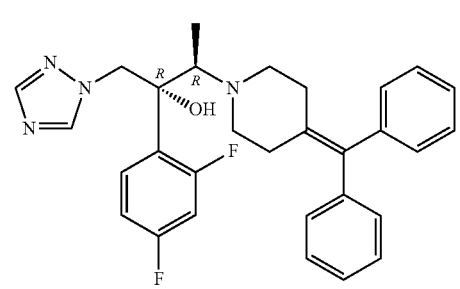

(IX)

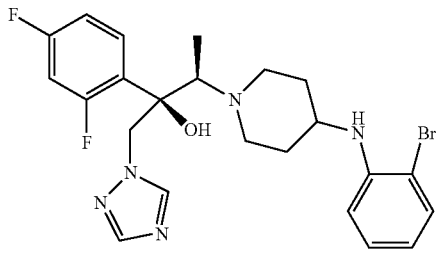

(X)

By way of example, starting from the compound of formula (V), the compounds of formula (VI), (VII) and (X) can easily be prepared by reductive amination; still by way of example, the preparation by reductive amination of the compound of formula (X) is illustrated in detail in the Experimental Section. Furthermore, the compound of formula (VIII) can be prepared by reduction of the double bond and subsequent activation for a nucleophilic substitution, whereas the compound of formula (IX) can be prepared by a Wittig or McMurry reaction as already described for efinaconazole. All of the above mentioned reactions are well known to the skilled in the art who, having available the compound of formula (V) subject-matter of the present invention, is perfectly able to synthesize the molecules above.

Now the invention will be set forth in detail by the following examples that are in no way limiting the scope of protection.

EXPERIMENTAL SECTION

The equipment used for the analyses are the following:
UPLC: Acquity UPLC-SQD Waters
NMR: Avance Bruker 400 MHz

Example 1

Preparation of (2R,3R)-2-(2,4-difluorophenyl)-3-(1,4-dioxa-8-azaspiro[4.5]decanil)-1-(1H-1,2,4-triazol-1-il)-2-butanol (Compound of Formula (IV)

Figure 1:
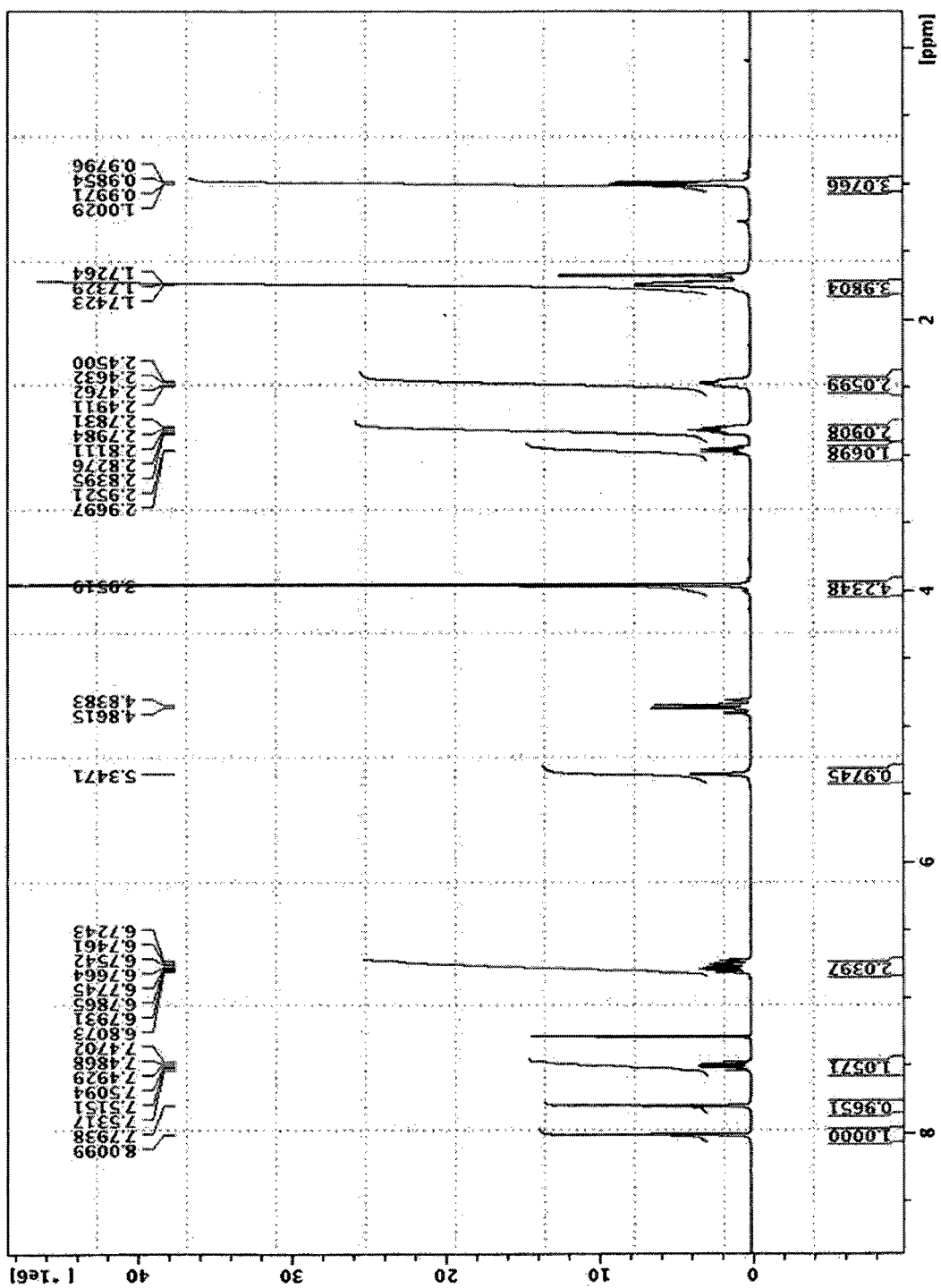
FIG. 1 depicts the NMR spectrum of the compound of formula (IV).

15 g compound of formula (II) is dissolved in 30 ml ethanol and 10 ml water, 23 ml compound of formula (III) is added and the mixture is heated at reflux until complete reaction (check at the end of the reaction by UPLC). Water is added until complete precipitation. The title product is filtered. Yield 20 g; UPLC purity higher than 99%. The NMR spectrum of the title compound is reported in FIG. 1, the mass is reported in FIG. 3 (top spectrum).

Example 2

Preparation of (2R,3R)-2-(2,4-difluorophenyl)-3-(4-oxo-1-piperidinyl)-1-(1H-1,2,4-triazol-1-il)-2-butanol (compound of formula (V)) in hydrated form as geminal diol 10 g compound of formula (IV) is dissolved in 200 ml 2 M HCl. The mixture is heated at 80° C. and maintained until complete reaction (check at the end of the reaction by UPLC). At the end the product is extracted in 100 ml dichloromethane, by adding NaOH until basic pH and is evaporated under vacuum. 9 g compound of formula (V) is isolated with chromatographic purity higher than 99%.

Figure 2:
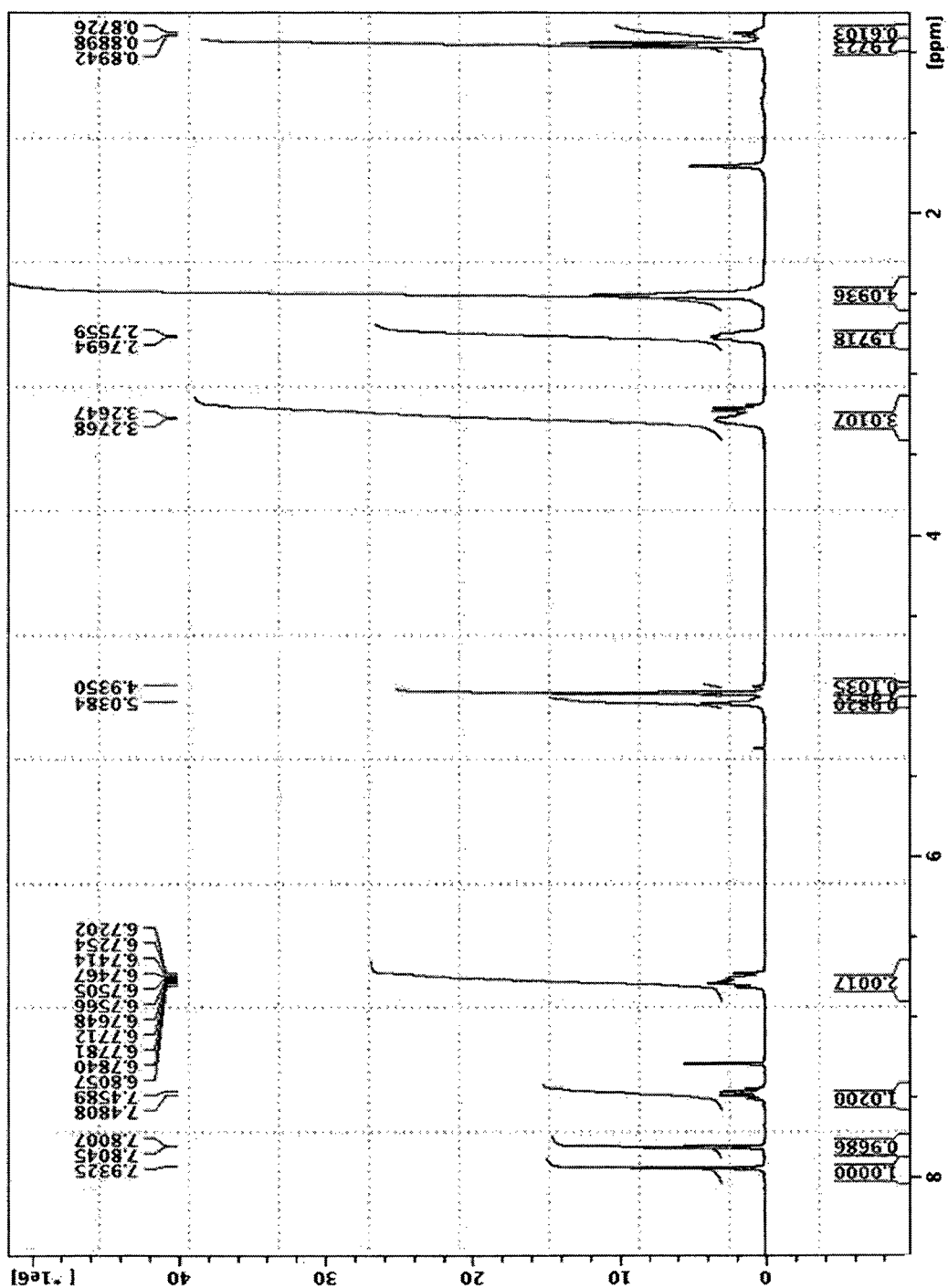
FIG. 2 depicts the NMR spectrum of the compound of formula (V).
Figure 3:
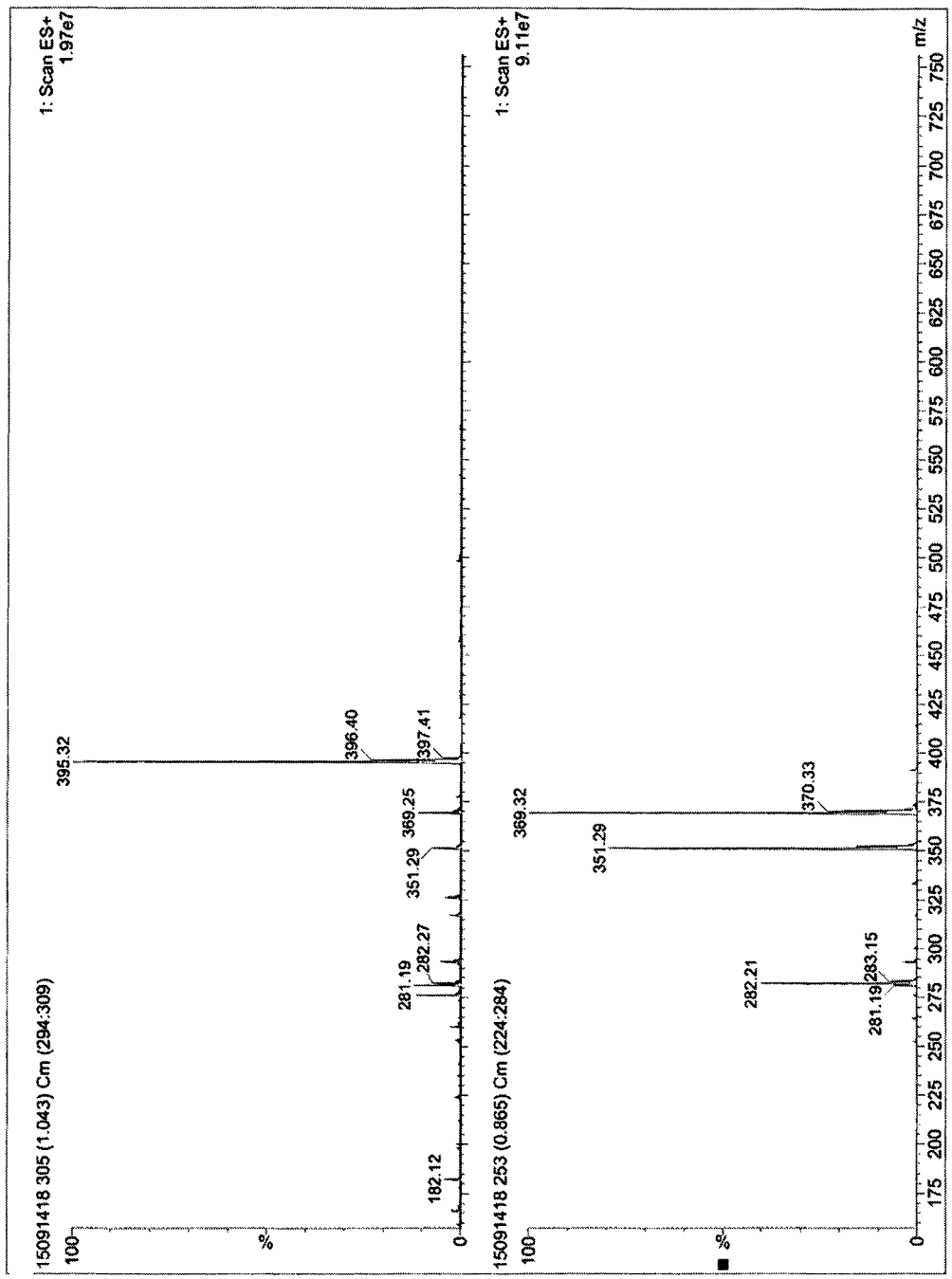
FIG. 3 depicts the mass spectra of the compounds of formula (IV) and (V).

The NMR spectrum of the title compound is reported in FIG. 2, the mass is reported in FIG. 3 (bottom spectrum).

Example 3

Preparation of Efinaconazole (Compound of Formula (I))—Wittig Reaction

In 9 ml toluene, 3 g triphenyl methyl phosphinyl bromide is reacted with 1.5 g potassium terbutylate. At ambient temperature, 1.9 g compound of formula (V) is added with further 9 ml toluene. It is maintained at ambient temperature and under stirring until complete reaction (check by UPLC). Thus, the reaction is quenched with 20 ml water and the phases are separated. The organic phase is acidified with 6N HCl and the toluene phase is eliminated. The product is re-extracted with 50 ml dichloromethane, by basifying with 10 N NaOH. Dichloromethane is evaporated and 1.2 g efinaconazole is obtained.

Example 4

Preparation of Efinaconazole (Compound of Formula (I))—McMurry Reaction 0.7 g compound of formula (V) is reacted in 6 ml dichloromethane and 4 ml THF with 0.39 g Mg and 0.75 g $TiCl_4$ at 0° C. It is maintained at ambient temperature and under stirring until complete reaction (check by UPLC). The reaction is quenched with 10 ml potassium carbonate saturated solution. The precipitate (salts) is filtrated and the organic phase is separated. Dichloromethane is evaporated under vacuum and 0.6 g efinaconazole is obtained.

Example 5

Figure 4:
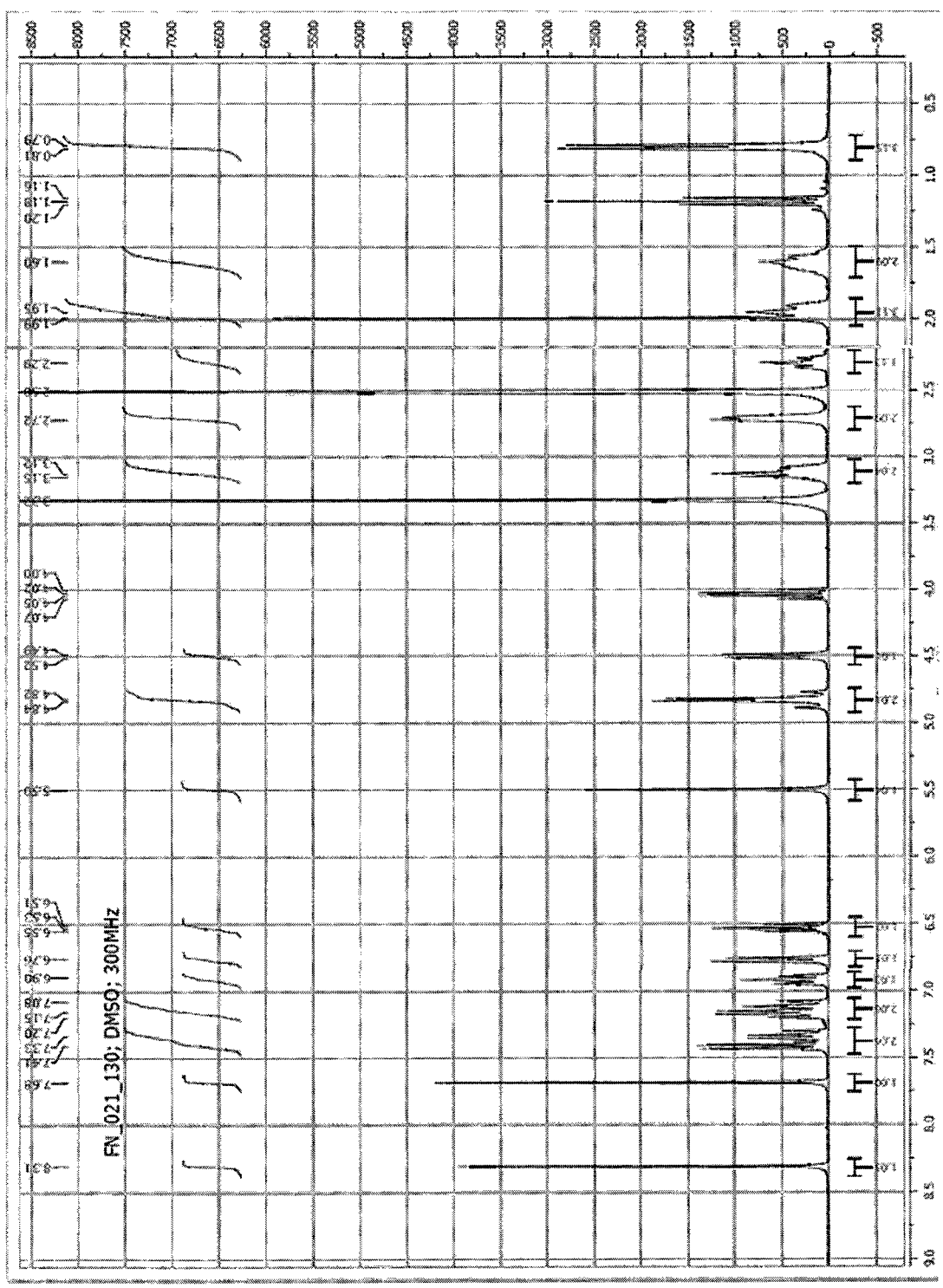
FIG. 4 depicts the NMR spectrum of the compound of formula (X).
Figure 5:
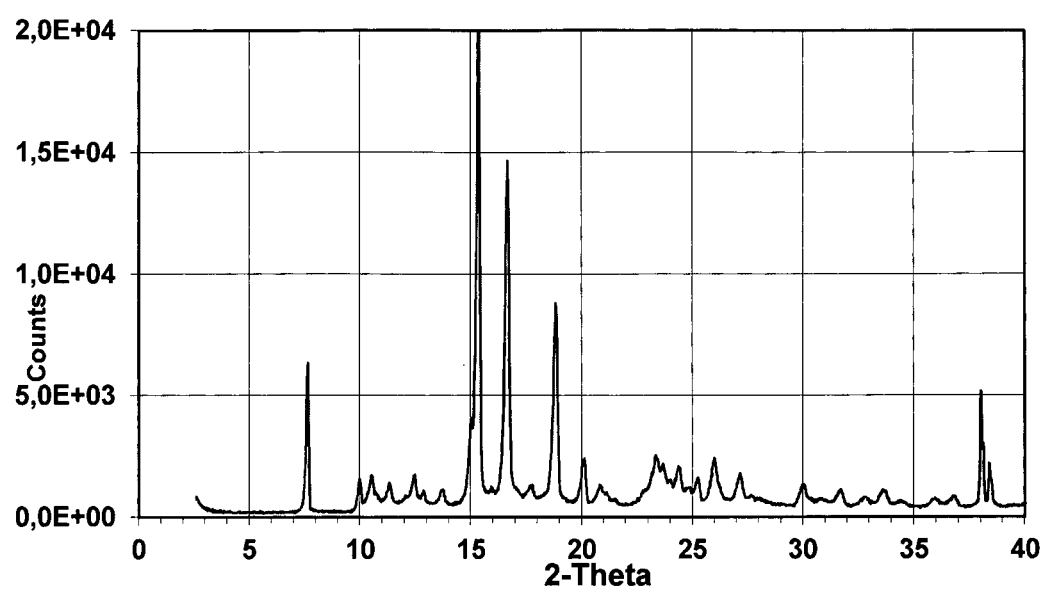
FIGS. 5 and 6 depict the X-ray diffraction patterns of efinaconazole obtained according to the invention.
Figure 6:
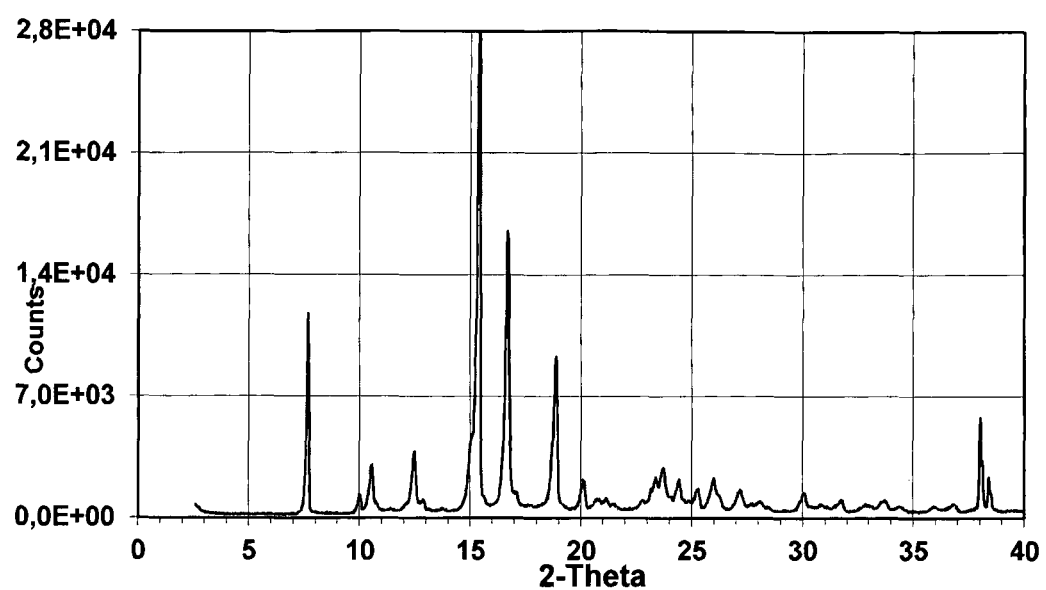

Preparation of (2R,3R)-2-(2,4-difluorophenyl)-3-[4-(2-bromophenyl-amino)-1-piperidinyl]-1-(1H-1,2,4-triazol-1-il)-2-butanol (Compound of Formula (X))—Reductive Amination 305 mg compound of formula (V) is reacted in 6 ml methanol and 1.6 ml acetic acid with 224.8 mg 2-bromoaniline. To this reaction, a solution made of 28.8 mg sodium cyanoborohydride in 4 ml methanol is slowly added. It is maintained at ambient temperature and under stirring until complete reaction (check by UPLC). The solution is concentrated under vacuum and 30 ml water and 10 ml ethyl acetate are added. The phases are separated and the organic phase is dried over sodium sulphate, finally the solvent is evaporated under vacuum, 354 mg title compound is obtained. The NMR spectrum of the title compound is reported in FIG. 4.

The invention claimed is:

1. A process for preparing a compound of formula (IV) and a compound of formula (V), salts, solvates and hydrates thereof

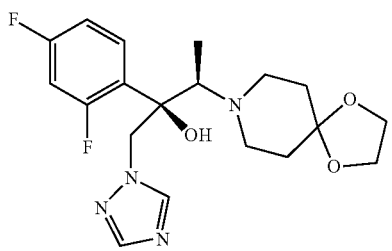
(IV)

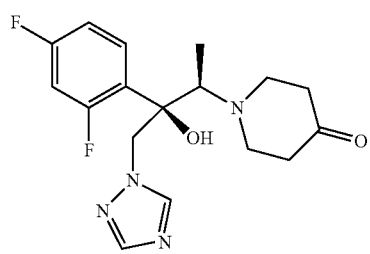
(V)

comprising (a) reacting compound of formula (II)

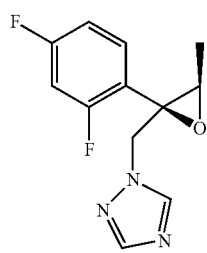
(II)

with compound of formula (III)

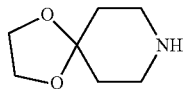
(III)

to obtain the compound of formula (IV), and optionally (b) hydrolyzing the compound of formula (IV), in an acidic environment, to give the compound of formula (V).

2. The process according to claim 1, wherein the step (a) is carried out in a mixture of a lower $C_1$-$C_4$ alcohol and water.

3. The process according to claim 2, wherein the step (a) is carried out in a mixture of ethanol and water.

4. The process according to claim 1, wherein the step (a) has a reaction temperature between 50° C. and 110° C.

5. The process according to claim 4, wherein said temperature is reflux temperature.

6. The process according to claim 1, wherein the step (b) is carried out in an aqueous solution of hydrochloric acid.

7. The process according to claim 5, wherein the step (b) has a reaction temperature of between 50° C. and the reflux temperature.

8. The process according to claim 7, wherein said temperature is 80° C.

9. The process according claim 1 wherein the compound of formula (II) is reacted with the compound of formula (III) in a solvent mixture containing about 25% water and about 75% ethanol, at the reflux temperature of the reaction mixture; subsequently, the compound (IV) is converted into compound (V) by acid hydrolysis, by heating in aqueous hydrochloric acid; said compound (V) being extracted from the aqueous phase by extracting in one or more organic solvents.

10. A compound selected from compound of formula (IV), salts, solvates or hydrates thereof

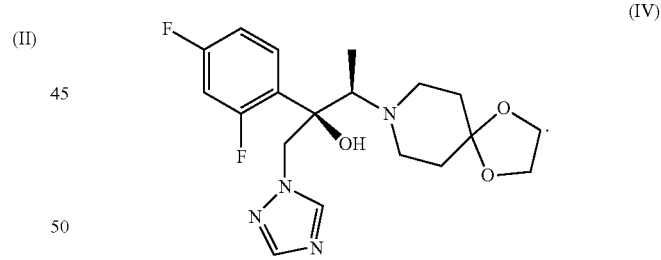
(IV)

* * * * *